United States Patent
Hayakawa et al.

(10) Patent No.: US 9,477,151 B2
(45) Date of Patent: Oct. 25, 2016

(54) ALICYCLIC ESTER COMPOUND, AND (METH)ACRYLIC COPOLYMER AND PHOTOSENSITIVE RESIN COMPOSITION CONTAINING SAME

(71) Applicant: Mitsubishi Gas Chemical Company, Inc., Tokyo (JP)

(72) Inventors: Shoichi Hayakawa, Mie (JP); Yoshio Nishimura, Chiba (JP); Kikuo Furukawa, Tokyo (JP); Hiroyasu Tanaka, Chiba (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 14/786,114

(22) PCT Filed: Apr. 22, 2014

(86) PCT No.: PCT/JP2014/061316
§ 371 (c)(1),
(2) Date: Oct. 21, 2015

(87) PCT Pub. No.: WO2014/175275
PCT Pub. Date: Oct. 30, 2014

(65) Prior Publication Data
US 2016/0070168 A1  Mar. 10, 2016

(30) Foreign Application Priority Data

Apr. 23, 2013 (JP) .................. 2013-090080
Feb. 14, 2014 (JP) .................. 2014-026210

(51) Int. Cl.
G03F 7/039 (2006.01)
C08F 220/28 (2006.01)
C07C 67/26 (2006.01)
C07C 69/757 (2006.01)
C08L 33/14 (2006.01)

(52) U.S. Cl.
CPC ............. *G03F 7/039* (2013.01); *C07C 67/26* (2013.01); *C07C 69/757* (2013.01); *C08F 220/28* (2013.01); *C08L 33/14* (2013.01); *C07C 2103/74* (2013.01); *C08F 2220/285* (2013.01)

(58) Field of Classification Search
None
See application file for complete search history.

(56) References Cited

U.S. PATENT DOCUMENTS

| 6,656,659 B1 | 12/2003 | Nozaki et al. |
| 7,556,908 B2 | 7/2009 | Takemoto et al. |
| 8,293,449 B2 | 10/2012 | Iwai et al. |
| 2004/0191674 A1 | 9/2004 | Hanamoto et al. |
| 2005/0271974 A1 | 12/2005 | Rahman et al. |
| 2013/0023638 A1 | 1/2013 | Furukawa et al. |

FOREIGN PATENT DOCUMENTS

| CN | 1550894 A | 12/2004 |
| CN | 1961260 A | 5/2007 |
| CN | 102884094 A | 1/2013 |
| JP | H4-39665 A | 2/1992 |
| JP | H10-319595 A | 12/1998 |
| JP | 2000-26446 A | 1/2000 |
| JP | 2000-122295 A | 4/2000 |
| JP | 2003-167346 A | 6/2003 |
| JP | 2004-323704 A | 11/2004 |
| JP | 2005-331918 A | 12/2005 |
| JP | 2006-243474 A | 9/2006 |
| JP | 2007-210961 A | 8/2007 |
| JP | 2011-123143 A | 6/2011 |
| JP | 2012-128009 A | 7/2012 |
| WO | 2012/008546 A1 | 1/2012 |

OTHER PUBLICATIONS

International Search Report date of mailing May Jul. 15, 2014 for PCT/JP2014/061316 and English translation of the same. (2 pages).
Furukawa, Seki, Kozawa and Tagawa; "Evaluation of adamantane derivatives for chemically amplified resist—a comparison between Arf, EUV and EB exposures—"; SPIE, vol. 6923-692334 (2008), pp. 1-12.

*Primary Examiner* — Cynthia Hamilton
(74) *Attorney, Agent, or Firm* — Fitch, Even, Tabin & Flannery LLP

(57) ABSTRACT

The present invention provides, as a chemically amplified resist, a well-balanced resist or compound which results in improved sensitivity, resolution and line edge roughness (LER) without impairing the fundamental physical properties required as a resist (e.g., pattern shape, dry etching resistance, heat resistance). A mixture of cycloaliphatic ester compounds represented by general formulae (1) to (3), and a process for preparation thereof, as well as a (meth)acrylic copolymer comprising the cycloaliphatic ester compounds of general formulae (1) to (3) and a photosensitive resin composition thereof are provided.

8 Claims, No Drawings

ALICYCLIC ESTER COMPOUND, AND (METH)ACRYLIC COPOLYMER AND PHOTOSENSITIVE RESIN COMPOSITION CONTAINING SAME

CROSS-REFERENCE TO RELATED APPLICATIONS

This application is a U.S. national phase application filed under 35 U.S.C. §371 of International Application PCT/JP2014/061316, filed on Apr. 22, 2014, designating the United States, which claims priority from Japanese Application Number 2013-090080, filed Apr. 23, 2013 and Japanese Application Number 2014-026210, filed Feb. 14, 2014, which are hereby incorporated herein by reference in their entirety.

TECHNICAL FIELD

The present invention relates to novel cycloaliphatic ester compounds which can be used as starting materials for optical materials (e.g., resists for KrF, ArF and F2 excimer lasers, chemically amplified resists for X-rays, electron beams or EUV (extreme ultraviolet rays)), for resin compositions excellent in heat resistance, chemical resistance and light transmittance, and for other various industrial resin compositions, and also relates to (meth)acrylic copolymers and photosensitive resin compositions comprising the same.

BACKGROUND ART

In response to the increasing capacity of flash memory, a type of storage device, and to expansion of the market for image sensors or the like designed for high-resolution cameras in mobile phones and smartphones, there arises a strong demand for high-density integration in semiconductor devices. In the manufacture of these various electronic devices, photolithographic techniques are used widely. In photolithography, efforts have been made to facilitate high-density integration by using a light source of shorter wavelength. When a KrF excimer laser or a short wavelength light source developed thereafter is used as a light source, chemically amplified resists are used in most cases and they are generally configured in the form of solutions containing a functional resin serving as a base material and a photoacid generator and further containing several types of additives. Among these components, a functional resin serving as a base material is a determinant of resist performance and it is important for such a functional resin to have a good balance of various properties including etching resistance, substrate adhesion, transparency against a light source to be used, rate of development, etc.

Functional resins for use in photoresists for KrF excimer lasers are usually polymers comprising, e.g., a vinyl compound or acrylate as a repeating unit. For example, poly(hydroxystyrene) type resins have been proposed in the case of resists for KrF excimer laser lithography (Patent Document 1), while acrylic resins whose backbone is composed of adamantyl (meth)acrylate have been proposed in the case of resists for ArF excimer laser lithography (Patent Documents 2 to 6); and hence the required backbone is now being fixed. However, polymers composed of a single type of repeating unit are not used for this purpose. This is because a single type of repeating unit cannot satisfy all of the properties including etching resistance. In actual cases, several types, i.e., two or more types of repeating units having functional groups required to improve the individual properties are used for copolymerization to give a functional resin, and the resulting functional resin is further blended with a photoacid generator and others and dissolved in a solvent for use as a photosensitive resin composition.

Recent lithographic processes have further facilitated high-density integration. ArF excimer laser lithography has continued to progress from immersion exposure to double patterning exposure, while various efforts have also been made to develop extreme ultraviolet (EUV) lithography, which receives attention as a next-generation lithographic technique, and direct writing with electron beams.

Under circumstances where developmental efforts for high-density integration have been continued, it is shown that the content of alcoholic hydroxyl groups contained in a resin composition tends to improve the sensitivity and/or resolution (see Non-patent Document 1). As an example of a resin comprising a monomer with an alcoholic hydroxyl group, a resin comprising 3,5-dihydroxy-1-adamantyl (meth)acrylate has also been proposed, by way of example (see Patent Document 7). Moreover, there is also a report showing that a chemically amplified positive resist composition which contains a resin whose repeating unit comprises a (meth)acrylic acid ester derivative having a linker introduced thereinto and an acid generator is not only good in various resist performance including resolution, but also achieves good line edge roughness (Patent Document 8).

However, to fulfill the requirement for high-density integration at 20 nm and beyond, further improvements in performance are essential, and there is a demand for further increases in the sensitivity and resolution of resists. On the other hand, when simply improving the sensitivity alone, there will arise new problems of reduced resolution and poor line edge roughness. For this reason, further studies are now conducted on resins for acid diffusion control and on combinations with various photoacid generators in an attempt to make further improvements.

Moreover, although there is knowledge of how to prepare glycerine carboxylic acid diesters (Patent Document 9), this document does not disclose a cycloaliphatic ester compound of specific structure available for use in photosensitive resin compositions and a process for preparation of this compound.

PRIOR ART DOCUMENTS

Patent Documents

Patent Document 1: Japanese Laid-Open Patent Publication No. 2006-243474

Patent Document 2: Japanese Laid-Open Patent Publication No. H4-39665

Patent Document 3: Japanese Laid-Open Patent Publication No. H10-319595

Patent Document 4: Japanese Laid-Open Patent Publication No. 2000-26446

Patent Document 5: Japanese Laid-Open Patent Publication No. 2003-167346

Patent Document 6: Japanese Laid-Open Patent Publication No. 2004-323704

Patent Document 7: Japanese Laid-Open Patent Publication No. 2000-122295

Patent Document 8: Japanese Laid-Open Patent Publication No. 2005-331918
Patent Document 9: Japanese Laid-Open Patent Publication No. 2007-210961

Non-Patent Documents

Non-patent Document 1: SPIE, 6923-123 (2008)

SUMMARY OF THE INVENTION

Under these circumstances, there is a strong demand for the development of a photosensitive resin composition which can achieve improved sensitivity, resolution and line edge roughness without adversely affecting the fundamental properties required as a photosensitive resin composition.

The present invention aims to prepare, as a chemically amplified resist responsive to KrF excimer lasers, ArF excimer lasers, F2 excimer lasers, X-rays, electron beams or EUV, a well-balanced resist which results in improved sensitivity, resolution and line edge roughness (LER) without impairing the fundamental physical properties required as a resist (e.g., pattern shape, dry etching resistance, heat resistance), thereby providing a compound adaptable to future developed techniques for high-density integration of semiconductor integrated circuits.

As a result of extensive and intensive efforts made to solve each of the problems stated above, the inventors of the present invention have found that a mixture of cycloaliphatic ester compounds represented by general formulae (1) to (3) and photosensitive resin compositions comprising the same as a repeating unit not only achieve good sensitivity, but also improve various resist performance including resolution and line edge roughness in lithographic operations conducted with KrF excimer lasers, ArF excimer lasers, F2 excimer lasers, X-rays, electron beams or EUV (extreme ultraviolet rays), and hence these compounds are useful compounds that can be expected to solve each of the above problems associated with high-density integration of semiconductor integrated circuits. This finding led to the completion of the present invention. Moreover, the present invention includes a process for preparing a mixture of the above cycloaliphatic ester compounds, and this preparation process allows efficient preparation of the above cycloaliphatic ester compounds in high yields.

Namely, the present invention relates to a mixture of cycloaliphatic ester compounds represented by general formulae (1) to (3), and a process for preparation thereof, as well as a (meth)acrylic copolymer comprising cycloaliphatic ester compounds represented by general formulae (1) to (3) and a photosensitive resin composition thereof.

More specifically, the present invention is as follows.
(I) A mixture, which comprises a cycloaliphatic ester compound represented by the following general formula (1), a cycloaliphatic ester compound represented by the following general formula (2) and a cycloaliphatic ester compound represented by the following general formula (3):

[Formula 1]

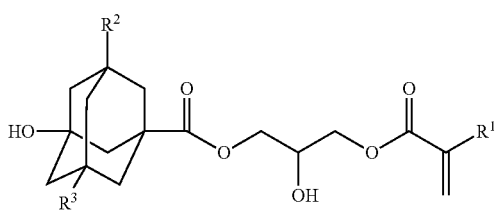

(1)

[Formula 2]

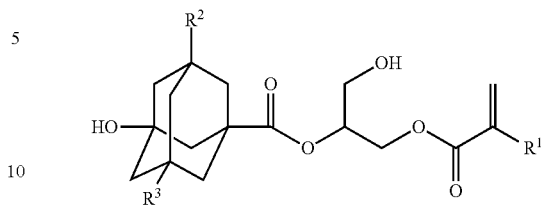

(2)

[Formula 3]

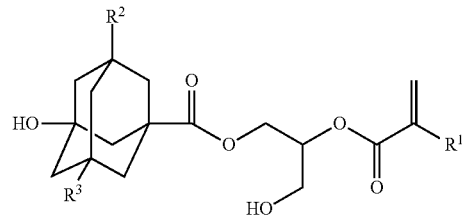

(3)

(wherein $R^1$ represents a hydrogen atom or a methyl group, and $R^2$ and $R^3$, which may be the same or different, each independently represent a hydrogen atom, a hydroxyl group, a cyclic or linear or branched alkyl group containing 1 to 10 carbon atoms, an aryl group, a cycloalkyl group, an alkoxy group containing 1 to 10 carbon atoms, an aryloxy group, an acyloxy group containing 2 to 6 carbon atoms, or a halogen group).

(II) A process for preparing the mixture of cycloaliphatic ester compounds according to (I) above, which comprises a reaction of an adamantane compound represented by general formula (4) with a glycidyl (meth)acrylate compound represented by general formula (5):

[Formula 4]

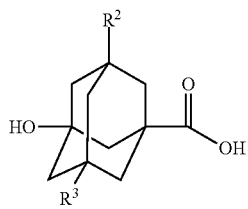

(4)

(wherein $R^2$ and $R^3$ are as defined in general formulae (1) to (3))

[Formula 5]

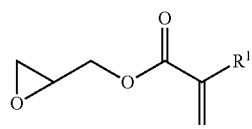

(5)

(wherein $R^1$ represents a hydrogen atom or a methyl group).
(III) The process according to (II) above, wherein the glycidyl (meth)acrylate compound represented by general formula (5) is reacted in an amount ranging from 0.50 to 0.99 equivalents relative to the adamantane compound represented by general formula (4).

(IV) A (meth)acrylic copolymer, which comprises at least one of the following general formulae (6) to (8) as a repeating unit:

[Formula 6]

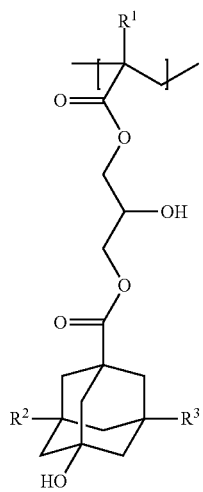

(6)

[Formula 7]

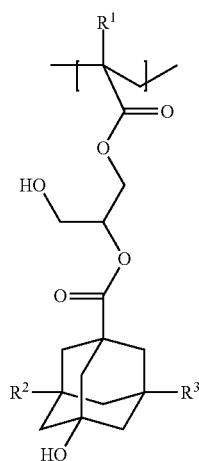

(7)

[Formula 8]

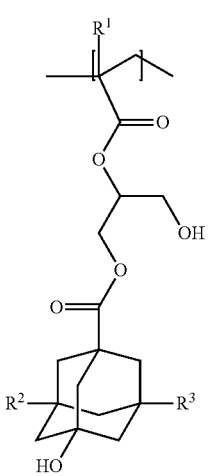

(8)

(wherein $R^1$, $R^2$ and $R^3$ are as defined in general formulae (1) to (3)).

(V) The (meth)acrylic copolymer according to (IV) above, which comprises at least one selected from the above general formulae (6) to (8), at least one selected from the following general formulae (9) to (10), and at least one selected from general formulae (11) to (12) as repeating units:

[Formula 9]

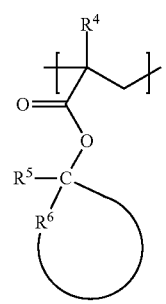

(9)

(wherein $R^4$ represents a hydrogen atom or a methyl group, $R^5$ represents an alkyl group containing 1 to 4 carbon atoms, and $R^6$ represents a linear or branched alkylene or cycloaliphatic alkylene group containing 5 to 20 carbon atoms)

[Formula 10]

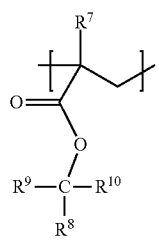

(10)

(wherein $R^7$ represents a hydrogen atom or a methyl group, $R^8$ and $R^9$, which may be the same or different, each independently represent an alkyl group containing 1 to 4 carbon atoms, and $R^{10}$ represents a cycloalkyl or cycloaliphatic alkyl group containing 5 to 20 carbon atoms)

[Formula 11]

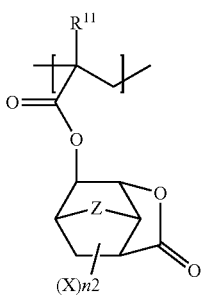

(11)

(wherein $R^{11}$ represents a hydrogen atom or a methyl group, Z represents methylene (—$CH_2$—) or oxa (—O—), each X may be the same or different and represents a hydroxyl group, a halogen group, a nitrile group, a carboxylic acid group, an alkyl carboxylate group containing 1 to 4 carbon atoms, or an alkoxide group containing 1 to 4 carbon atoms, and n2 represents an integer of 0 to 2)

[Formula 12]

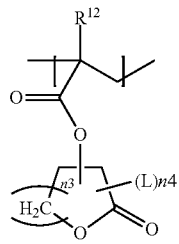

(12)

(wherein $R^{12}$ represents a hydrogen atom or a methyl group, n3 represents an integer of 1 to 3, L represents a methyl group, an ethyl group, a hydroxyl group or a halogen group, and n4 represents 0 to 2).

(VI) A photosensitive resin composition, which comprises the (meth)acrylic copolymer according to (IV) or (V) above and a photoacid generator.

(VII) The mixture according to (I) above, which comprises 40% to 80% of the cycloaliphatic ester compound of general formula (1), 10% to 30% of the cycloaliphatic ester compound of general formula (2), and 10% to 30% of the cycloaliphatic ester compound of general formula (3).

The cycloaliphatic ester compounds of the present invention are preferred for use as starting materials for various resin compositions of various functional polymers designed based on heat resistance, surface hardness, chemical resistance and/or lipophilic properties. In particular, when used as copolymer components of chemically amplified resists for KrF excimer lasers, ArF excimer lasers, F2 excimer lasers, X-rays, electron beams or EUV (extreme ultraviolet rays), the cycloaliphatic ester compounds of the present invention achieve improved resolution and line edge roughness.

DESCRIPTION OF EMBODIMENTS

The present invention will be further described in more detail below. The cycloaliphatic ester compounds of the present invention are represented by the following general formulae (1) to (3):

[Formula 13]

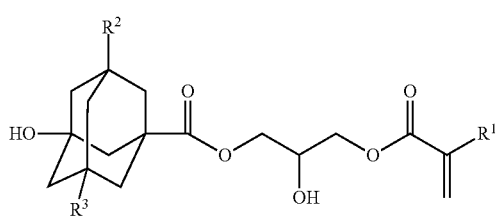

(1)

[Formula 14]

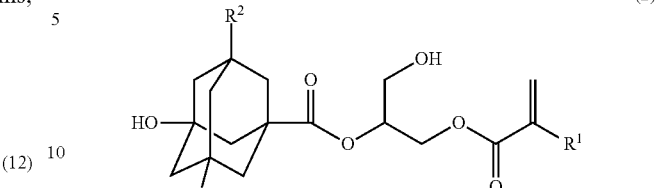

(2)

[Formula 15]

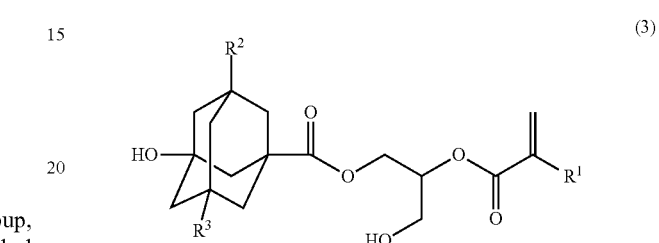

(3)

(wherein $R^1$ represents a hydrogen atom or a methyl group, and $R^2$ and $R^3$, which may be the same or different, each independently represent a hydrogen atom, a hydroxyl group, a cyclic or linear or branched alkyl group containing 1 to 10 carbon atoms, an aryl group, a cycloalkyl group, an alkoxy group containing 1 to 10 carbon atoms, an aryloxy group, an acyloxy group containing 2 to 6 carbon atoms, or a halogen group).

The cycloaliphatic ester compounds of the present invention represented by general formulae (1) to (3) may be obtained by a reaction of an adamantane compound represented by general formula (4) with a glycidyl (meth)acrylate compound represented by general formula (5) in the presence of an amine or a salt thereof serving as a catalyst. The cycloaliphatic ester compounds of the present invention represented by general formulae (1) to (3) are in tautomeric relationship with each other and usually obtained in a state of a mixture of the cycloaliphatic ester compounds represented by general formulae (1) to (3).

[Formula 16]

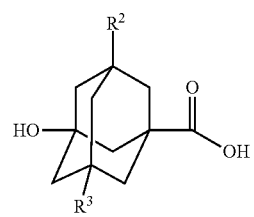

(4)

(wherein $R^2$ and $R^3$ are as defined in general formulae (1) to (3))

[Formula 17]

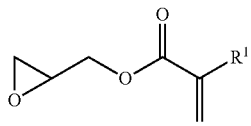

(5)

(wherein R¹ represents a hydrogen atom or a methyl group).

Specific examples of the cycloaliphatic ester compound of the present invention represented by the above general formula (1) include those represented by the chemical formulae shown below, i.e., 2-hydroxy-3-(meth)acryloyloxypropyl 3-hydroxy-1-adamantanecarboxylate, 2-hydroxy-3-(meth)acryloyloxypropyl 3-hydroxy-5,7-dimethyl-1-adamantanecarboxylate, 2-hydroxy-3-(meth)acryloyloxypropyl 3-hydroxy-5-ethyl-1-adamantanecarboxylate, 2-hydroxy-3-(meth)acryloyloxypropyl 3,5-dihydroxy-1-adamantanecarboxylate, etc.

[Formula 18]

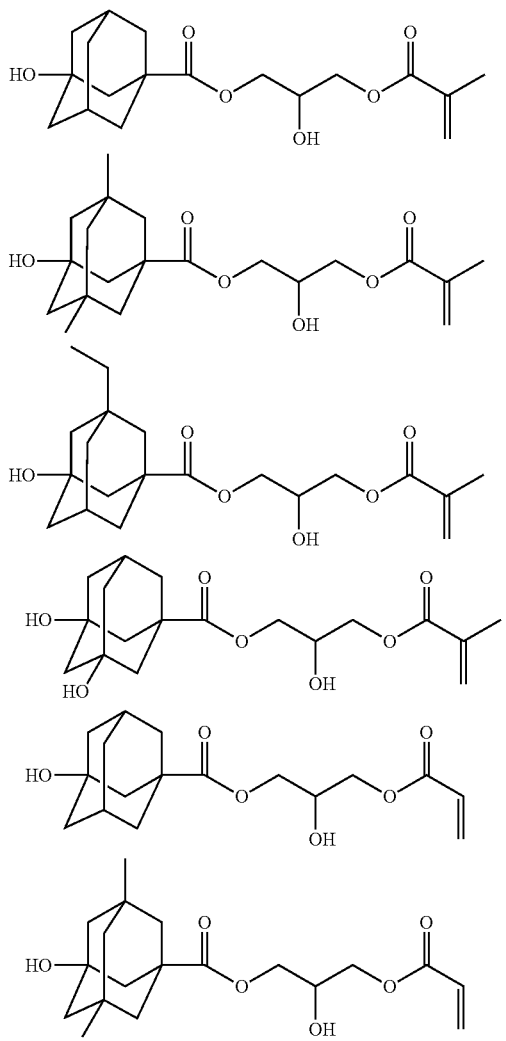

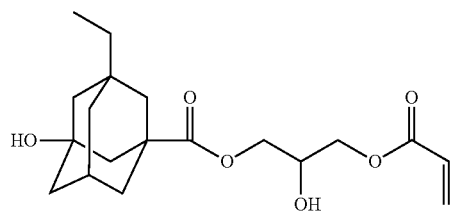

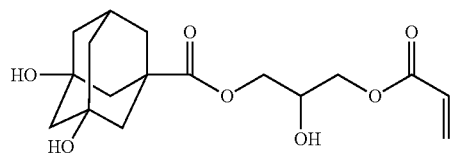

Specific examples of the cycloaliphatic ester compound of the present invention represented by the above general formula (2) include those represented by the chemical formulae shown below, i.e., 1-hydroxy-3-(meth)acryloyloxypropan-2-yl 3-hydroxy-1-adamantanecarboxylate, 1-hydroxy-3-(meth)acryloyloxypropan-2-yl 3-hydroxy-5,7-dimethyl-1-adamantanecarboxylate, 1-hydroxy-3-(meth)acryloyloxypropan-2-yl 3-hydroxy-5-ethyl-1-adamantanecarboxylate, 1-hydroxy-3-(meth)acryloyloxypropan-2-yl 3,5-dihydroxy-1-adamantanecarboxylate, etc.

[Formula 19]

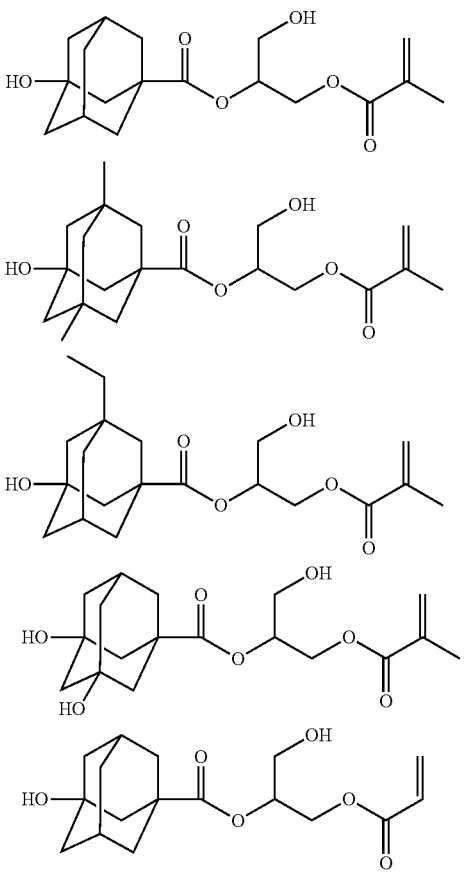

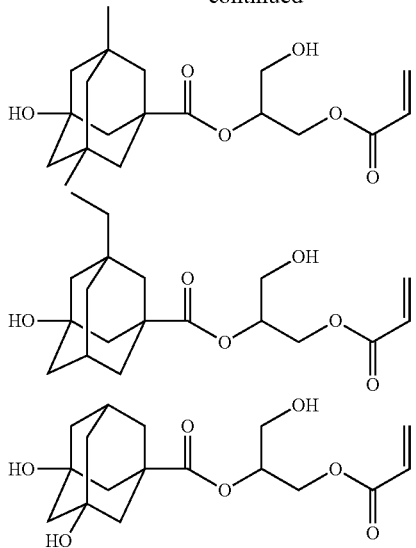

Likewise, specific examples of the cycloaliphatic ester compound of the present invention represented by the above general formula (3) include those represented by the chemical formulae shown below, i.e., 3-hydroxy-2-(meth)acryloyloxypropyl 3-hydroxy-1-adamantanecarboxylate, 3-hydroxy-2-(meth)acryloyloxypropyl 3-hydroxy-5,7-dimethyl-1-adamantanecarboxylate, 3-hydroxy-2-(meth)acryloyloxypropyl 3-hydroxy-5-ethyl-1-adamantanecarboxylate, 3-hydroxy-2-(meth)acryloyloxypropyl 3,5-dihydroxy-1-adamantanecarboxylate, etc.

[Formula 20]

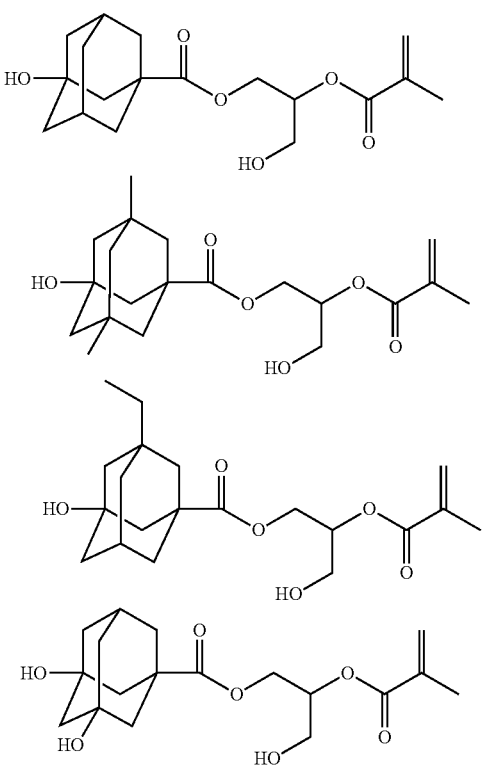

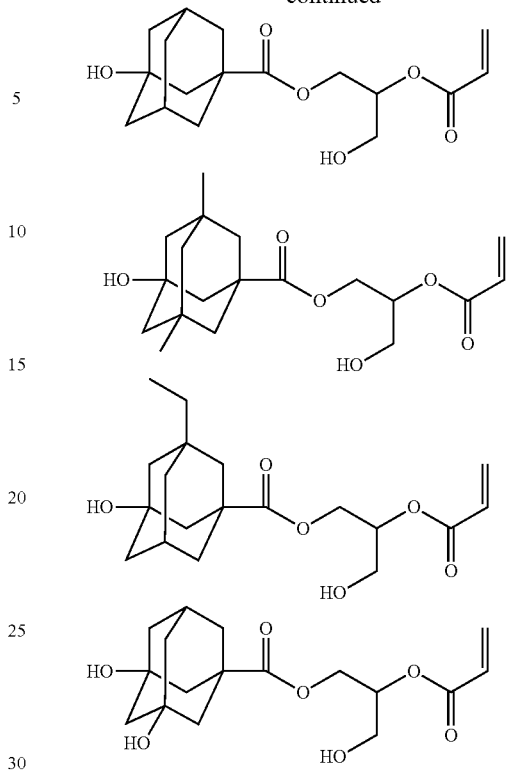

The mixture of the cycloaliphatic ester compounds of the present invention preferably comprises 40% to 80% of the cycloaliphatic ester compound of general formula (1), 10% to 30% of the cycloaliphatic ester compound of general formula (2), and 10% to 30% of the cycloaliphatic ester compound of general formula (3). More preferably, the mixture of the cycloaliphatic ester compounds of the present invention comprises 50% to 75% of the cycloaliphatic ester compound of general formula (1), 15% to 25% of the cycloaliphatic ester compound of general formula (2), and 15% to 25% of the cycloaliphatic ester compound of general formula (3).

Specific examples of the adamantane compound represented by general formula (4) available for use in the present invention include 3-hydroxy-1-adamantanecarboxylic acid, 5-methyl-3-hydroxy-1-adamantanecarboxylic acid, 5,7-dimethyl-3-hydroxy-1-adamantanecarboxylic acid, 3,5-dihydroxy-1-adamantanecarboxylic acid, 5-ethyl-3-hydroxy-1-adamantanecarboxylic acid, and 3,5,7-trihydroxy-1-adamantanecarboxylic acid.

Specific examples of the glycidyl (meth)acrylate compound represented by general formula (5) for use in the present invention include glycidyl acrylate and glycidyl methacrylate. The amount to be added is desirably less than 1 equivalent relative to the adamantane compound represented by general formula (4). If the amount is 1 equivalent or more, transesterification will occur during reaction and/or purification to thereby generate a di(meth)acrylic ester having two (meth)acrylic groups as a by-product. When monomers rich in di(meth)acrylic esters are used to prepare polymers, the performance of the resulting resists will be reduced. The amount to be added ranges from 0.50 to 0.99 equivalents, preferably 0.80 to 0.95 equivalents, relative to the adamantane compound. If the amount is less than this range, the adamantane compound represented by general formula (4) remains unreacted in abundance, which is economically unfavorable.

As an onium salt, an amine or a salt thereof serving as a catalyst for use in the reaction between the adamantane compound represented by general formula (4) and the glycidyl (meth)acrylate compound represented by general formula (5), a commonly used quaternary ammonium salt or a less nucleophilic amine may be used. Specific examples include tetramethylammonium chloride, tetramethylammonium bromide, tetramethylammonium iodide, tetraethylammonium chloride, tetraethylammonium bromide, tetraethylammonium iodide, tetrapropylammonium chloride, tetrapropylammonium bromide, tetrabutylammonium chloride, tetrabutylammonium bromide, benzyltrimethylammonium chloride, benzyltrimethylammonium bromide, benzyltributylammonium chloride, benzyltributylammonium bromide, phenyltrimethylammonium chloride, 2-chloro-1-methylpyridinium iodide, 1-butylpyridinium chloride, methylviologen chloride, 1,8-diazabicyclo[5.4.0]undec-7-ene, 1,5-diazabicyclo[4.3.0]non-5-ene, and 2,6-lutidine. Although there is no particular difference in their reactivity, the reaction will not proceed unless a sufficient amount of a catalyst is dissolved in a solvent. For this reason, it is necessary to select an amine or a salt thereof which can be dissolved in a solvent to be used. These amines or salts thereof may be used either alone or as a mixture of two or more of them. The amount of an amine(s) or a salt(s) thereof to be added ranges from 0.001 to 10 equivalents, preferably 0.01 to 1 equivalent, more preferably 0.05 to 0.5 equivalents, relative to the adamantane compound. If the amount is 0.001 equivalents or more, the reaction will be completed with sufficient rapidity, whereas amines or salts thereof are difficult to separate and purify if their amount is 10 equivalents or more.

In the present invention, solvents for use in the reaction between the adamantane compound represented by general formula (4) and the glycidyl (meth)acrylate compound represented by general formula (5) may be exemplified by dimethyl sulfoxide, diethyl ether, diisopropyl ether, tetrahydrofuran, dioxane, dimethylformamide, chloroform, chlorobenzene, acetone, methyl ethyl ketone, and methyl isobutyl ketone. Among them, dimethyl sulfoxide is desired because it allows sufficient dissolution of the adamantane compound represented by general formula (4) and also allows elevation of the reaction temperature due to its high boiling point. These solvents may be used either alone or as a mixture of two or more solvents. The amount of a solvent(s) to be used is 1 to 100 parts by mass, preferably 3 to 10 parts by mass, relative to 1 part by mass of the adamantane compound represented by general formula (4), although it is desirable to ensure complete dissolution of the adamantane compound represented by general formula (4). If the adamantane compound is not dissolved completely, side reactions will be more likely to occur. Moreover, due to low reactivity of this reaction, it is desirable to conduct the reaction at a concentration as high as possible. For this purpose, preparation may also be accomplished in a solvent-free system in cases where the adamantanecarboxylic acid compound represented by general formula (4), the glycidyl (meth)acrylate compound represented by general formula (5), and an amine(s) or a salt(s) thereof are dissolved and mixed together.

As to detailed conditions of the above reaction, appropriate conditions should be determined depending on the substrate concentration and the type of catalyst to be used, although the above reaction may generally be conducted at a reaction temperature of 20° C. to 150° C., preferably 50° C. to 120° C., for a reaction time of 1 hour to 10 hours, preferably 2 hours to 8 hours, and under normal, reduced or elevated pressure. Moreover, the reaction may be conducted in any known mode selected as appropriate from batch, semi-batch and continuous modes, etc.

In addition, a polymerization inhibitor may be added during the above reaction. Any polymerization inhibitor may be used for this purpose, and examples include nitroso compounds such as 2,2,6,6-tetramethyl-4-hydroxypiperidine-1-oxyl, N-nitrosophenylhydroxylamine ammonium salt, N-nitrosophenylhydroxylamine aluminum salt, N-nitroso-N-(1-naphthyl)hydroxylamine ammonium salt, N-nitrosodiphenylamine, N-nitroso-N-methylaniline, nitrosonaphthol, p-nitrosophenol, and N,N'-dimethyl-p-nitrosoaniline; sulfur-containing compounds such as phenothiazine, methylene blue, and 2-mercaptobenzoimidazole; amines such as N,N'-diphenyl-p-phenylenediamine, N-phenyl-N'-isopropyl-p-phenylenediamine, 4-hydroxydiphenylamine, and aminophenol; quinones such as hydroxyquinoline, hydroquinone, methylhydroquinone, p-benzoquinone, and hydroquinone monomethyl ether; phenols such as p-methoxyphenol, 2,4-dimethyl-6-t-butylphenol, catechol, 3-s-butylcatechol, and 2,2-methylenebis-(6-t-butyl-4-methylphenol); imides such as N-hydroxyphthalimide; oximes such as cyclohexane oxime and p-quinone dioxime; dialkyl thiodipropionates and so on. The amount to be added is 0.001 to 10 parts by weight, preferably 0.01 to 1 part by weight, relative to 100 parts by weight of the above glycidyl (meth)acrylate compound.

The cycloaliphatic ester compounds represented by general formulae (1) to (3) obtained on the basis of the foregoing descriptions may be used after being isolated into their respective isomers, although isomerization reaction will occur after isolation to thereby generate a mixture. For this reason, these compounds may be provided directly in a mixture state without being isolated from each other, e.g., for use in polymerization of resist polymers. However, resist monomers are generally required to have a lower content of metal impurities, and it is therefore desirable to isolate and purify them as desired high purity monomers by known purification techniques, e.g., filtration, concentration, distillation, extraction, crystallization, recrystallization, column chromatography, separation and purification with the use of activated carbon or the like, or any combination of these techniques. More specifically, the reaction mixture may be washed with water to remove excess (meth)acrylic acid derivatives and additives such as acids and bases. In this case, the water used for washing may comprise an appropriate inorganic salt such as sodium chloride or sodium hydrogen carbonate. Moreover, the unreacted (meth)acrylic acid derivatives and others are removed by washing with alkaline. For alkaline washing, aqueous sodium hydroxide, aqueous potassium hydroxide, aqueous sodium carbonate, aqueous sodium hydrogen carbonate, aqueous ammonia or the like may be used, although there is no particular limitation on the alkaline component to be used. Further, acid washing may be conducted to remove metal impurities. For acid washing, inorganic acids such as aqueous hydrochloric acid, aqueous sulfuric acid and aqueous phosphoric acid, or organic acids such as aqueous oxalic acid may be used. During washing, an organic solvent or the like may be added to the reaction mixture. The organic solvent to be added may be the same as used for the reaction, or alternatively, a different organic solvent may be used for this purpose. However, it is generally preferable to use a less polar solvent which ensures good separation from water.

(Meth)acrylic copolymers obtained by copolymerization of the cycloaliphatic ester compounds of the present invention represented by general formulae (1) to (3) may be used in functional resins for use in photoresists. During copolymerization of the cycloaliphatic ester compounds represented by general formulae (1) to (3) to obtain (meth)acrylic copolymers, these compounds may be used either alone or as a mixture.

The (meth)acrylic copolymers of the present invention preferably comprise at least one selected from general formulae (6) to (8), at least one selected from general formulae (9) to (10), and at least one selected from general formulae (11) to (12) as repeating units. It should be noted that the repeating units of general formulae (6) to (8) may be obtained from the cycloaliphatic ester compounds represented by general formulae (1) to (3), respectively, upon polymerization as starting materials (monomers).

[Formula 21]

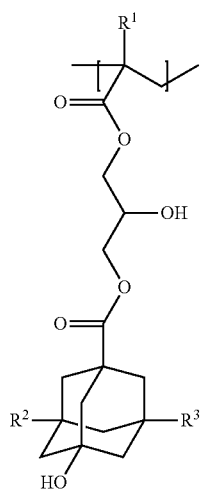

(6)

[Formula 22]

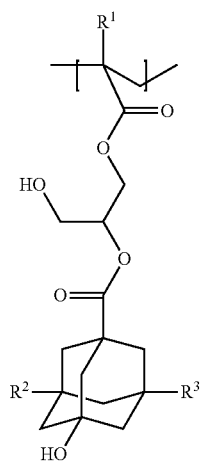

(7)

[Formula 23]

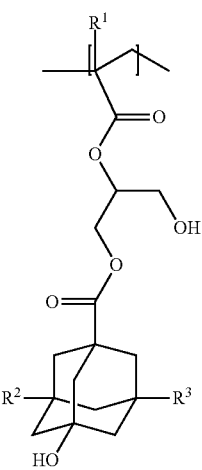

(8)

(wherein $R^1$, $R^2$ and $R^3$ are as defined in general formulae (1) to (3))

[Formula 24]

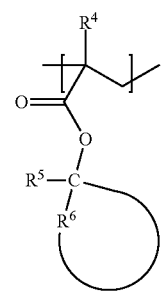

(9)

(wherein $R^4$ represents a hydrogen atom or a methyl group, $R^5$ represents an alkyl group containing 1 to 4 carbon atoms, and $R^6$ represents a linear or branched alkylene or cycloaliphatic alkylene group containing 5 to 20 carbon atoms)

[Formula 25]

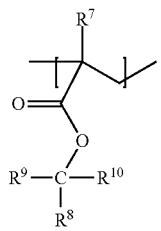

(10)

(wherein $R^7$ represents a hydrogen atom or a methyl group, $R^8$ and $R^9$, which may be the same or different, each represent an alkyl group containing 1 to 4 carbon atoms, and $R^{10}$ represents a cycloalkyl or cycloaliphatic alkyl group containing 5 to 20 carbon atoms)

[Formula 26]

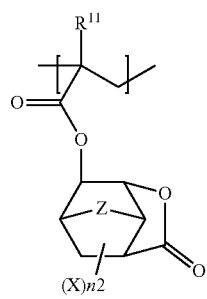

(11)

(wherein $R^{11}$ represents a hydrogen atom or a methyl group, Z represents methylene (—CH$_2$—) or oxa (—O—), each X may be the same or different and represents a hydroxyl group, a halogen group, a nitrile group, a carboxylic acid group, an alkyl carboxylate group containing 1 to 4 carbon atoms, or an alkoxide group containing 1 to 4 carbon atoms, and n2 represents 0 to 2)

[Formula 27]

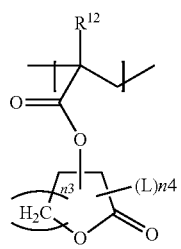

(12)

(wherein $R^{12}$ represents a hydrogen atom or a methyl group, n3 represents 1 to 3, L represents a methyl group, an ethyl group, a hydroxyl group or a halogen group, and n4 represents 0 to 2).

Examples of a starting material for the repeating unit represented by general formula (9) include 2-methyl-2-(meth)acryloyloxyadamantane, 2-ethyl-2-(meth)acryloyloxyadamantane, 2-isopropyl-2-(meth)acryloyloxyadamantane, 2-n-propyl-2-(meth)acryloyloxyadamantane, 2-n-butyl-2-(meth)acryloyloxyadamantane, 1-methyl-1-(meth)acryloyloxycyclopentane, 1-ethyl-1-(meth)acryloyloxycyclopentane, 1-methyl-1-(meth)acryloyloxycyclohexane, 1-ethyl-1-(meth)acryloyloxycyclohexane, 1-methyl-1-(meth)acryloyloxycycloheptane, 1-ethyl-1-(meth)acryloyloxycycloheptane, 1-methyl-1-(meth)acryloyloxycyclooctane, 1-ethyl-1-(meth)acryloyloxycyclooctane, 2-ethyl-2-(meth)acryloyloxydecahydro-1,4:5,8-dimethanonaphthalene, 2-ethyl-2-(meth)acryloyloxynorbornane and so on.

Examples of a starting material for the repeating unit represented by general formula (10) include 2-cyclohexyl-2-(meth)acryloyloxypropane, 2-(4-methylcyclohexyl)-2-(meth)acryloyloxypropane, 2-adamantyl-2-(meth)acryloyloxypropane, 2-(3-(1-hydroxy-1-methylethyl)adamantyl)-2-(meth)acryloyloxypropane and so on.

Examples of a starting material for the repeating unit represented by general formula (11) include 2-(meth)acryloyloxy-5-oxo-4-oxatricyclo[4.2.1.0$^{3,7}$]nonane, 7- or 8-(meth)acryloyloxy-3-oxo-4-oxatricyclo[5.2.1.0$^{2,6}$]decane, 9-(meth)acryloyloxy-3-oxo-2-oxa-6-oxa-tricyclo[4.2.1.0$^{4,8}$]nonane, 2-(meth)acryloyloxy-5-oxo-4-oxa-8-oxatricyclo[4.2.1.0$^{3,7}$]nonane, 2-(meth)acryloyloxy-9-methoxycarbonyl-5-oxo-4-oxatricyclo[4.2.1.0$^{3,7}$]nonane, 2-(meth)acryloyloxy-5-oxo-4-oxatricyclo[4.2.1.0$^{3,7}$] nonane-6-carbonitrile and so on.

Examples of a starting material for the repeating unit represented by general formula (12) include α-(meth)acryloyloxy-γ-butyrolactone, β-(meth)acryloyloxy-γ-butyrolactone, (meth)acryloyloxypantolactone and so on.

The repeating units represented by general formulae (9) and (10) have the function of being dissociated by the action of an acid. These repeating units are almost equal in their performance, and as a result of comprising at least one of them, reaction will occur with an acid generated from a photoacid generator upon exposure to thereby produce a carboxylic acid group, which allows conversion into an alkali-soluble form.

Likewise, the repeating units represented by general formulae (11) and (12) each have a lactone group, and these repeating units have almost the same function. This function is to improve the solubility in a solvent, the adhesion to a substrate and the affinity to an alkaline developer as a result of comprising at least one of these repeating units, and thereby allows the use for photolithographic purposes.

With regard to the copolymerization ratio in (meth)acrylic copolymers consisting of the repeating units represented by general formulae (6) to (8), general formulae (9) to (10) and general formulae (11) to (12), the repeating units of general formulae (6) to (8) constitute 1% by weight to 60% by weight, preferably 3% by weight to 50% by weight, more preferably 5% by weight to 40% by weight of the repeating units, at least one of the compounds of general formulae (9) to (10) constitutes 10% by weight to 80% by weight, preferably 15% by weight to 60% by weight, more preferably 20% by weight to 50% by weight of the repeating units, and at least one of the compounds of general formulae (11) to (12) constitutes 10% by weight to 80% by weight, preferably 15% by weight to 60% by weight, more preferably 15% by weight to 50% by weight.

It should be noted that the total copolymerization ratio of general formulae (6) to (8), general formulae (9) to (10) and general formulae (11) to (12) is set to 100% by weight. Moreover, the (meth)acrylic copolymers of the present invention may further comprise other repeating units at a copolymerization ratio of 20% by weight or less, more preferably 10% by weight or less, in addition to the repeating units of general formula (6) to (12).

In general, polymerization may be accomplished as follows: monomers which form repeating units are dissolved in a solvent and reacted in the presence of a catalyst under heating or cooling conditions. Conditions used for the polymerization reaction may optionally be determined depending on the type of initiator, the method of initiation (e.g., thermal or photo), temperature, pressure, concentration, the type of solvent, the type of additive(s), etc. In the case of the (meth)acrylic copolymers of the present invention, their polymerization may be accomplished in a known manner, e.g., by radical polymerization using a radical generator (e.g., azoisobutyronitrile, peroxide), ionic polymerization using a catalyst (e.g., alkyllithium, Grignard reagent), etc.

Examples of a solvent for use in the polymerization reaction of the (meth)acrylic copolymers of the present invention include ketones such as 2-butanone, 2-heptanone, methyl isobutyl ketone, and cyclohexanone; alkanes such as hexane, heptane, octane, cyclohexane, cyclooctane, decalin, and norbornane; alcohols such as methanol, ethanol, propanol, 2-propanol, n-butanol, sec-butanol, t-butanol, pentanol, hexanol, and propylene glycol monomethyl ether; ethers such as diethyl ether, tetrahydrofuran, and 1,4-dioxane; as well as carboxylic acid esters such as ethyl acetate, butyl acetate, methyl lactate, and propylene glycol monomethyl ether acetate. These solvents may be used either alone or as a mixture of two or more of them.

The (meth)acrylic copolymers of the present invention, e.g., (meth)acrylic copolymers comprising any of the above repeating units of general formulae (6) to (12) may be random copolymers, block copolymers or graft copolymers, with random copolymers being preferred.

The (meth)acrylic copolymers obtained in the present invention may be purified in a known manner. More specifically, for removal of metal impurities, ultrafiltration, microfiltration, washing with acid, washing with water having an electric conductivity of 10 mS/m or less, and extraction may be conducted in any combination. In the case of washing with acid, acids to be added include water-soluble acids, i.e., organic acids such as formic acid, acetic acid and propionic acid, as well as inorganic acids such as hydrochloric acid, sulfuric acid, nitric acid and phosphoric acid, with inorganic acids being preferred for use in terms of good separation from the reaction mixture. Likewise, for removal of oligomers, ultrafiltration, microfiltration, crystallization, recrystallization, extraction, washing with water having an electric conductivity of 10 mS/m or less and so on may be conducted in any combination.

The (meth)acrylic copolymers of the present invention have a weight average molecular weight calculated as polystyrene (hereinafter referred to as "Mw") of preferably 1,000 to 500,000, more preferably 3,000 to 100,000, as measured by gel permeation chromatography (GPC). Moreover, with regard to the ratio between Mw and number average molecular weight calculated as polystyrene (hereinafter referred to as "Mn") as measured by GPC, the (meth)acrylic copolymers generally have a Mw/Mn ratio of 1 to 10, preferably 1 to 5. Further, in the present invention, the (meth)acrylic copolymers may be used either alone or as a mixture of two or more of them.

In the photosensitive resin composition of the present invention, the above (meth)acrylic polymer(s) and a photoacid generator may be used by being dissolved in a solvent. Examples of a solvent commonly used for this purpose include linear ketones such as 2-pentanone and 2-hexanone; cyclic ketones such as cyclopentanone and cyclohexanone; propylene glycol monoalkyl acetates such as propylene glycol monomethyl ether acetate and propylene glycol monoethyl ether acetate; ethylene glycol monoalkyl ether acetates such as ethylene glycol monomethyl ether acetate and ethylene glycol monoethyl ether acetate; propylene glycol monoalkyl ethers such as propylene glycol monomethyl ether and propylene glycol monoethyl ether; ethylene glycol monoalkyl ethers such as ethylene glycol monomethyl ether and ethylene glycol monoethyl ether; diethylene glycol alkyl ethers such as diethylene glycol dimethyl ether and diethylene glycol diethyl ether; esters such as ethyl acetate and ethyl lactate; alcohols such as cyclohexanol and 1-octanol; as well as ethylene carbonate, γ-butyrolactone and so on. These solvents may be used either alone or as a mixture of two or more of them.

Depending on the wavelength of exposure light, a photoacid generator may be selected as appropriate from among those available for use as acid generators in chemically amplified resist compositions, in consideration of the range of resist coating thickness and the light absorption coefficient of the photoacid generator per se. Such photoacid generators may be used either alone or in combination of two or more of them. The amount of an acid generator(s) to be used is preferably 0.1 to 20 parts by weight, more preferably 0.5 to 15 parts by weight, relative to 100 parts by weight of the (meth)acrylic copolymer(s).

Examples of photoacid generators available for use in the far ultraviolet region include onium salt compounds, sulfonimide compounds, sulfone compounds, sulfonic acid ester compounds, quinone diazide compounds and diazomethane compounds, etc. Among them, onium salt compounds are preferred for KrF excimer lasers, EUV and electron beams, as exemplified by sulfonium salts, iodonium salts, phosphonium salts, diazonium salts, pyridinium salts, etc. Specific examples include triphenylsulfonium triflate, triphenylsulfonium nonafluorobutyrate, triphenylsulfonium hexafluoroantimonate, triphenylsulfonium naphthalenesulfonate, (hydroxyphenyl)benzylmethylsulfonium toluenesulfonate, diphenyliodonium triflate, diphenyliodonium pyrenesulfonate, diphenyliodonium dodecylbenzenesulfonate, diphenyliodonium hexafluoroantimonate and so on.

The photosensitive resin composition of the present invention may further comprise an acid diffusion inhibitor having the ability to prevent an acid(s) generated from the acid generator(s) upon exposure from diffusing into the resist coating and thereby inhibit unfavorable chemical reactions in the non-exposed regions. An acid diffusion inhibitor preferred for this purpose is a nitrogen-containing organic compound whose basicity is not affected by exposure and/or thermal treatment during resist pattern formation. Examples of such a nitrogen-containing organic compound include monoalkylamines such as n-hexylamine, n-heptylamine, and n-octylamine; dialkylamines such as di-n-butylamine; trialkylamines such as triethylamine; substituted trialcoholamines such as triethanolamine, tripropanolamine, tributanolamine, tripentanolamine, and trihexanolamine; trialkoxyalkylamines such as trimethoxyethylamine, trimethoxypropylamine, trimethoxybutylamine, and triethoxybutylamine; aromatic amines such as aniline, N,N-dimethylaniline, 2-methylaniline, 3-methylaniline, 4-methylaniline, 4-nitroaniline, and diphenylamine; amine compounds such as ethylenediamine; amide compounds such as formamide, N,N-dimethylformamide, N,N-dimethylacetamide, and N-methylpyrrolidone; urea compounds such as urea; imidazoles such as imidazole and benzimidazole; pyridines such as pyridine and 4-methylpyridine; as well as 1,4-diazabicyclo[2.2.2]octane and so on. The content of an acid diffusion inhibitor is generally 15 parts by weight or less, preferably 0.001 to 10 parts by weight, more preferably 0.005 to 5 parts by weight, relative to 100 parts by weight of the (meth)acrylic copolymer(s).

Furthermore, the photosensitive resin composition of the present invention may also optionally comprise various additives which have also been used in conventional chemically amplified resist compositions, as exemplified by surfactants, quenchers, sensitizers, antihalation agents, storage stabilizers, defoaming agents and so on.

To form a resist pattern from the photosensitive resin composition of the present invention, the composition solution prepared as described above may be applied onto a substrate (e.g., silicon wafer, metal, plastic, glass, ceramic) using an appropriate means such as a spin coater, a dip coater, a roller coater or the like to thereby form a resist coating, which is optionally pre-baking at a temperature around 50° C. to 200° C. before exposure through a mask pattern. The thickness of the coating is, for example, about 0.01 to 5 µm, preferably about 0.02 to 1 µm, and more preferably about 0.02 to 0.1 µm. For exposure, light of various wavelengths, e.g., ultraviolet rays, X-rays and the like may be used. For example, far ultraviolet rays (e.g., an $F_2$ excimer laser (wavelength: 157 nm), an ArF excimer laser (wavelength: 193 nm), a KrF excimer laser (wavelength: 248 nm)), EUV (wavelength: 13 nm), X-rays, electron beams or the like may be selected as appropriate for use as a light source. Moreover, exposure conditions including the amount of exposure may be determined as appropriate, depending on the components and their ratio in the photosensitive resin composition, the type of each additive, etc.

In the present invention, for stable formation of high-resolution patterns, post-exposure baking may preferably be conducted at a temperature of 50° C. to 200° C. for 30 seconds or longer after exposure. In this case, at a temperature of less than 50° C., the sensitivity will more widely vary depending on the type of substrate. The thermal treatment may be followed by development with an alkaline developer generally under conditions of 10° C. to 50° C. for 10 to 200 seconds, preferably 20° C. to 25° C. for 15 to 1200 seconds, to thereby form a desired resist pattern.

For use as the above alkaline developer, an alkaline compound such as an alkali metal hydroxide, aqueous ammonia, an alkylamine, an alkanolamine, a heterocyclic amine, a tetraalkylammonium hydroxide, choline, 1,8-diazabicyclo-[5.4.0]-7-undecene or 1,5-diazabicyclo-[4.3.0]-5-nonene may generally be dissolved at a concentration of 0.0001% to 10% by weight, preferably 0.01% to 5% by weight, more preferably 0.1% to 3% by weight, to prepare an aqueous alkaline solution. Moreover, the above developer composed of an aqueous alkaline solution may further comprise a water-soluble organic solvent and/or a surfactant, as required.

The photosensitive resin composition of the present invention is excellent in adhesion to a substrate and is soluble in alkalis, and allows pattern formation with high accuracy.

EXAMPLES

The present invention will be further described in more detail by way of the following examples, although the present invention is not limited in any way by the following examples. In the examples, it should be noted that novel (meth)acrylic compounds were determined for their purity and yield by high performance liquid chromatography (HPLC) and determined for their structure by $^1$H- and $^{13}$C-NMR. Confirmation of dimethacrylic forms was conducted by gas chromatography (GC) and gas chromatograph mass spectrometry. Measurement conditions for HPLC are as follows.
<HPLC Measurement Conditions>
Column: L-column ODS L-C18 (5 µm, 4.6φ×250 mm, Chemicals Evaluation and Research Institute, Japan); developing solvent: acetonitrile/water=40/60 (v/v); flow rate: 1 ml/minute; column temperature: 40° C.; detector: RI
<GC Conditions>
Column: TC-17 (0.53 mm I.D.×30 m); injection temperature: 280° C., oven temperature: 70° C. (kept for 1 minute) →elevated at 10° C./minute→280° C. (kept for 10 minutes); detector: FID; mobile phase: helium Example 1

Preparation of methacryloyloxyhydroxypropyl 3-hydroxy-1-adamantanecarboxylate

Into a 1000 ml three-necked round-bottomed flask equipped with a stirrer, a thermometer and an air inlet, 3-hydroxy-1-adamantanecarboxylic acid (49.08 g, 0.25 mol), glycidyl methacrylate (31.98 g, 0.225 mol), tetramethylammonium chloride (2.74 g, 25 mmol), p-methoxyphenol (319.6 mg, 2.6 mmol) and dimethyl sulfoxide (250 g) were introduced and stirred at 90° C. for 5 hours under air blowing conditions. After completion of the reaction, chloroform (1000 g) was added to the reaction mixture and the organic layer was washed with 5% aqueous sodium chloride (1000 g), 5% aqueous sodium carbonate (1000 g), 1% aqueous sulfuric acid (1000 g) and then 5% aqueous sodium chloride (1000 g). The organic layer was collected and silica gel (25 g) was added thereto, followed by stirring for 1 hour. The silica gel was removed with a 5C filter paper and washed with chloroform (1000 g). To the collected chloroform solutions, activated carbon (Kuraray Coal GLC10/32, 60 g) was added, followed by removal of the activated carbon with a 5C filter paper. The solvent was concentrated in vacuo to obtain a light-yellow viscous liquid (54.75 g, yield: 64.8%). Upon structural confirmation by H- and $^{13}$C-NMR and HPLC, the resulting product was confirmed to be a mixture of 2-hydroxy-3-methacryloyloxypropyl 3-hydroxy-1-adamantanecarboxylate (i.e., a compound of formula (1)), 1-hydroxy-3-methacryloyloxypropan-2-yl 3-hydroxy-1-adamantanecarboxylate (i.e., a compound of formula (2)) and 3-hydroxy-2-methacryloyloxypropyl 3-hydroxy-1-adamantanecarboxylate (i.e., a compound of formula (3)). Upon analysis by GC to confirm the generated amount of dimethacrylic forms, the ratio of dimethacrylic form/methacryloyloxyhydroxypropyl 1-hydroxy-3-adamantanecarboxylate was found to be 0.002. In addition, the ratio of the compounds of formulae (1), (2) and (3) was confirmed to be 64:18:18 from the NMR spectra and the area values in HPLC.

$^1$H-NMR spectrum (CDCl$_3$): δ 1.5 to 2.1 ppm (16H, adamantane), 1.9 ppm (3H, methyl group in the methacryloyl group), 3.7 ppm (0.75H, glycidyl group —C$\underline{H}_2$—OH in the structures of formulae (2) and (3)), 4.0 to 4.7 ppm (3.88H, glycidyl group), 5.1 ppm (0.37H, 2-position of the glycidyl group in the structures of formulae (2) and (3)), 5.6 ppm (1H, double bond in the methacryloyl group), 6.1 ppm (1H, double bond in the methacryloyl group).

$^{13}$C-NMR spectrum (CDCl$_3$): 18 ppm (methyl group in the methacryloyl group), 24.5 to 46.0 ppm (adamantane), 60.8 ppm, 61.0 ppm, 62.3 ppm, 62.8 ppm, 65.0 ppm, 67.7 ppm, 68.0 ppm, 72.0 ppm, 72.6 ppm (glycidyl group), 65.4 ppm (OH-substituted adamantane) 126.3 ppm (double bond end in the methacryloyl group) 135.8 ppm (α-position of carbonyl in the methacryloyl group), 166.8 ppm, 167.0 ppm, 167.3 ppm (carbonyl in the methacryloyl group), 176.0 ppm, 176.2 ppm, 176.4 ppm (carbonyl in adamantanecarboxylic acid).

Reference Example

The same procedure as shown in Example 1 was repeated, except that the amount of glycidyl methacrylate was changed to 49.75 g (0.35 mol). Upon analysis by GC to confirm the generated amount of dimethacrylic forms, the ratio of dimethacrylic form/methacryloyloxyhydroxypropyl 1-hydroxy-3-adamantanecarboxylate was found to be 0.072. In addition, the ratio of the compounds of formulae (1), (2) and (3) was confirmed to be 64:18:18 from the NMR spectra and the area values in HPLC.

Example 2

Preparation of methacryloyloxyhydroxypropyl 3-hydroxy-1-adamantanecarboxylate polymer The mixture of 2-hydroxy-3-methacryloyloxypropyl 3-hydroxy-1-adamantanecarboxylate (i.e., a compound of formula (1)), 1-hydroxy-3-methacryloyloxypropan-2-yl 3-hydroxy-1-adamantanecarboxylate (i.e., a compound of formula (2)) and 3-hydroxy-2-methacryloyloxypropyl 3-hydroxy-1-adamantanecarboxylate (i.e., a compound of formula (3)) obtained in Example 1 (hereinafter referred to as monomer M; 3.05 g), 2-ethyl-2-methacryloyloxyadamantane (hereinafter referred to as monomer E; 4.47 g) used as a starting material of formula (9), α-methacryloyloxy-γ-butyrolactone (hereinafter referred to as monomer G; 3.07 g) used as a starting material of formula (12), and azobisisobutyronitrile (0.37 g) were dissolved in tetrahydrofuran (90 mL) and polymerized for 15 hours under a nitrogen atmosphere while maintaining the reaction temperature at 60° C. (the initial monomer ratio M/E/G=20/40/40 mol %). After polymerization, the reaction mixture was added dropwise to 450 mL of n-hexane to thereby solidify and purify the resulting resin, and the generated white powder was filtered and dried overnight under reduced pressure at 40° C. to obtain methacrylic copolymer A (7.48 g).

Example 3

100 parts by weight of the methacrylic copolymer A and 10 parts by weight of triphenylsulfonium nonafluorobutanesulfonate (TPS-109, Midori Kagaku Co., Ltd., Japan) were dissolved in an ethyl lactate solvent to give a copolymer concentration of 6.3% by weight, thereby preparing photosensitive resin composition C. After an antireflection coating (ARC-29, Nissan Chemical Industries, Ltd., Japan) was applied onto a silicon wafer, this photoresist resin composition was applied onto the antireflection coating by spin coating to thereby form a photosensitive layer of 100 nm thickness. After pre-exposure bake on a hot plate at a temperature of 90° C. for 60 seconds, the photosensitive layer was irradiated in a 80 nm half-pitch line and space pattern (10 lines) using an electron beam lithography system (ELS-7700, Elionix Inc., Japan), followed by post-exposure bake (PEB) at a given temperature for 90 seconds. Then, the photosensitive layer was developed for 60 seconds with 0.3 M aqueous tetramethylammonium hydroxide and rinsed with pure water to obtain a line and space pattern.

Comparative Example 1

The same procedure as shown in Example 2 was repeated to obtain methacrylic copolymer B (6.85 g), except that the monomer M was replaced with 3-hydroxy-1-adamantyl methacrylate (hereinafter referred to as monomer H; 2.12 g) (the initial monomer ratio H/E/G=20/40/40 mol %).

Comparative Example 2

The same procedure as shown in Example 3 was repeated, except that 100 parts by weight of the methacrylic copolymer B and 10 parts by weight of triphenylsulfonium nonafluorobutanesulfonate (TPS-109, Midori Kagaku Co., Ltd., Japan) were dissolved in propylene glycol monomethyl ether acetate to give a copolymer concentration of 6.3% by weight, thereby preparing photosensitive resin composition D at a copolymer concentration of 6.3% by weight.

The resulting line and space patterns were observed by FE-SEM to determine their resolution and line edge roughness (LER). The results obtained are shown in Table 1. When compared at the same PEB temperature and at the same amount of exposure, the photosensitive resin composition C obtained in Example 3 was found to achieve better LER and a higher resolution than the photosensitive resin composition D obtained in Comparative Example 2.

TABLE 1

| Photosensitive resin composition | Copolymer | PEB temperature ° C. | Amount of exposure μC/cm² | Resolution nm | LER Nm |
|---|---|---|---|---|---|
| Example 3 | C | A | 90 | 10 | 88 | 8.1 |
| Comparative Example 2 | D | B | " | " | 93 | 10.9 |

Example 4

Preparation of methacryloyloxyhydroxypropyl 3-hydroxy-1-adamantanecarboxylate polymer 2

The mixture of 2-hydroxy-3-methacryloyloxypropyl 3-hydroxy-1-adamantanecarboxylate, 1-hydroxy-3-methacryloyloxypropan-2-yl 3-hydroxy-1-adamantanecarboxylate and 3-hydroxy-2-methacryloyloxypropyl 3-hydroxy-1-adamantanecarboxylate obtained in Example 1 (monomer M; 3.05 g), 2-adamantyl-2-methacryloyloxypropane (hereinafter referred to as monomer I; 4.72 g) used as a starting material represented by formula (10), 2-methacryloyloxy-5-oxo-4-oxatricyclo[4.2.1.0$^{3,7}$]nonane (hereinafter referred to as monomer N; 4.00 g) used as a starting material represented by formula (11), and azobisisobutyronitrile (0.37 g) were dissolved in tetrahydrofuran (100 mL) and polymerized for 15 hours under a nitrogen atmosphere while maintaining the reaction temperature at 60° C. (the initial monomer ratio M/I/N=20/40/40 mol %). After polymerization, the reaction mixture was added dropwise to 500 mL of n-hexane to thereby solidify and purify the resulting resin, and the generated white powder was filtered through a membrane filter and washed with n-hexane (1000 ml). The white powder was collected and dried overnight under reduced pressure at 40° C. to obtain methacrylic copolymer E (7.65 g).

Example 5

100 parts by weight of the methacrylic copolymer E and 10 parts by weight of triphenylsulfonium nonafluorobutanesulfonate (TPS-109, Midori Kagaku Co., Ltd., Japan) were dissolved in an ethyl lactate solvent to give a copolymer concentration of 6.3% by weight, thereby preparing photosensitive resin composition F.

Comparative Example 3

The same procedure as shown in Example 4 was repeated to obtain methacrylic copolymer G (7.43 g), except that the monomer M was replaced with 3-hydroxy-1-adamantyl methacrylate (monomer H; 2.12 g) (the initial monomer ratio H/I/N=20/40/40 mol %).

Comparative Example 4

100 parts by weight of the methacrylic copolymer G and 10 parts by weight of triphenylsulfonium nonafluorobutanesulfonate (TPS-109, Midori Kagaku Co., Ltd., Japan) were dissolved in an ethyl lactate solvent to give a copolymer concentration of 6.3% by weight, thereby preparing photosensitive resin composition H.

Examples 6 and 7 as well as Comparative Examples 5 and 6

Resist Pattern Formation

After an antireflection coating (ARC-29, Nissan Chemical Industries, Ltd., Japan) was applied onto a silicon wafer, the photosensitive resin composition C, D, F or H was applied by spin coating to form a photosensitive layer of 100 nm thickness for each case. The photosensitive layer formed from the photosensitive resin composition C (prepared in Example 3) was denoted as Example 6, the photosensitive layer formed from the photosensitive resin composition D (prepared in Comparative Example 2) was denoted as Comparative Example 5, the photosensitive layer formed from the photosensitive resin composition F (prepared in Example 5) was denoted as Example 7, and the photosensitive layer formed from the photosensitive resin composition H (prepared in Comparative Example 4) was denoted as Comparative Example 6. The results obtained for these examples are shown in Table 2. After pre-exposure bake on a hot plate at a temperature of 90° C. for 60 seconds, pattern exposure was conducted using an electron beam lithography system (ELS-7700, Elionix Inc., Japan), followed by post-exposure bake (PEB) at the temperature indicated in Table 2 for 90 seconds. Then, each photosensitive layer was developed for 60 seconds with 0.3 M aqueous tetramethylammonium hydroxide and rinsed with pure water to obtain a line and space pattern. The prepared line and space patterns were observed by FE-SEM. The amount of exposure required for resolution in a 100 nm 1:1 line and space pattern was determined as an optimum amount of exposure Eop ($\mu C/cm^2$), while the minimum size of a 1:1 line and space pattern separated and resolved at the optimum amount of exposure was determined as a highest resolution. Further, the space width was measured at 50 positions, and the results were used to determine the triple value ($3\sigma$) of standard deviation ($\sigma$), which was defined as LWR. The results obtained are shown in Table 2. Upon comparison of the results between Example 6 and Comparative Example 5, and between Example 7 and Comparative Example 6, the photosensitive resin compositions comprising the polymers of the present invention were confirmed to achieve better LWR and a smaller highest resolution.

TABLE 2

| | Photo sensitive resin composition | Monomers used | PEB [° C.] | Eop [$\mu C/cm^2$] | LWR [nm] | Highest resolution [nm] |
|---|---|---|---|---|---|---|
| Example 6 | C | M/E/G | 90 | 40 | 10.8 | 70 |
| Comparative Example 5 | D | H/E/G | 100 | 35 | 13.9 | 90 |
| Example 7 | F | M/I/N | 110 | 65 | 22.3 | 90 |
| Comparative Example 6 | H | H/I/N | 120 | 58 | 24.1 | 100 |

The invention claimed is:

1. A mixture, which comprises:
a cycloaliphatic ester compound represented by general formula (1);
a cycloaliphatic ester compound represented by general formula (2); and
a cycloaliphatic ester compound represented by general formula (3):

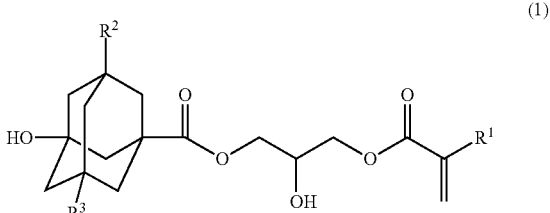

[Formula 1]
(1)

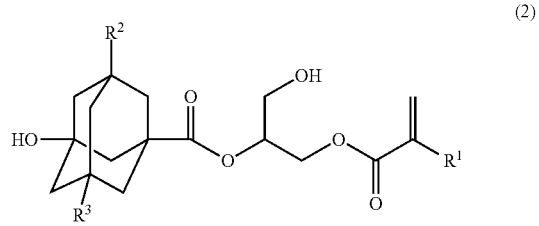

[Formula 2]
(2)

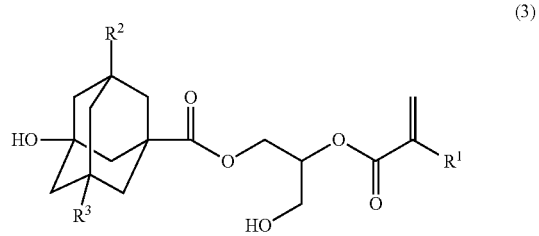

[Formula 3]
(3)

(wherein $R^1$ represents a hydrogen atom or a methyl group, and $R^2$ and $R^3$, which may be the same or different, each independently represent a hydrogen atom, a hydroxyl group, a cyclic or linear or branched alkyl group containing 1 to 10 carbon atoms, an aryl group, a cycloalkyl group, an alkoxy group containing 1 to 10 carbon atoms, an aryloxy group, an acyloxy group containing 2 to 6 carbon atoms, or a halogen group).

2. A process for preparing the mixture of cycloaliphatic ester compounds according to claim 1, which comprises a reaction of an adamantane compound represented by general formula (4) with a glycidyl (meth)acrylate compound represented by general formula (5):

[Formula 4]

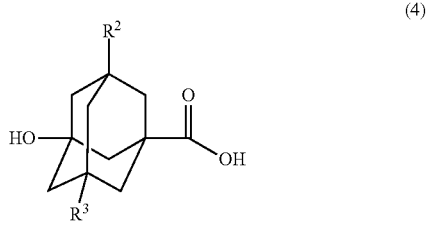

(4)

(wherein $R^2$ and $R^3$ are as defined in general formulae (1) to (3))

[Formula 5]

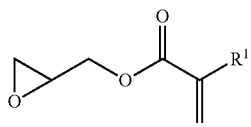

(5)

(wherein $R^1$ represents a hydrogen atom or a methyl group).

3. The process according to claim 2, wherein the glycidyl (meth)acrylate compound represented by general formula (5) is reacted in an amount ranging from 0.50 to 0.99 equivalents relative to the adamantane compound represented by general formula (4).

4. The mixture according to claim 1, which comprises 40% to 80% of the cycloaliphatic ester compound of general formula (1), 10% to 30% of the cycloaliphatic ester compound of general formula (2), and 10% to 30% of the cycloaliphatic ester compound of general formula (3).

5. A (meth)acrylic copolymer, which comprises at least one of general formulae (6) to (8) as a repeating unit:

[Formula 6]

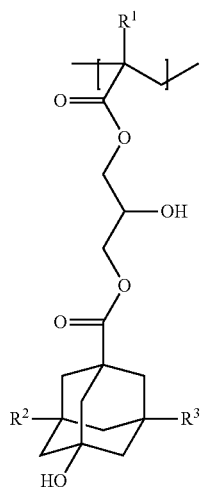

(6)

[Formula 7]

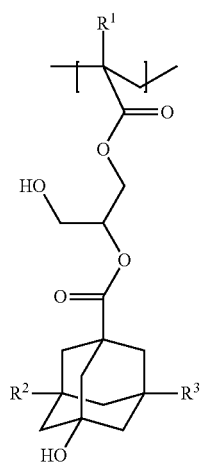

(7)

[Formula 8]

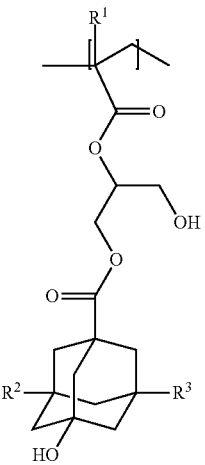

(8)

(wherein $R^1$ represents a hydrogen atom or a methyl group, and $R^2$ and $R^3$, which may be the same or different, each independently represent a hydrogen atom, a hydroxyl group, a cyclic or linear or branched alkyl group containing 1 to 10 carbon atoms, an aryl group, a cycloalkyl group, an alkoxy group containing 1 to 10 carbon atoms, an aryloxy group, an acyloxy group containing 2 to 6 carbon atoms, or a halogen group.

6. The (meth)acrylic copolymer according to claim 5, which comprises at least one selected from general formulae (6) to (8), at least one selected from general formulae (9) to (10), and at least one selected from general formulae (11) to (12) as repeating units:

[Formula 9]

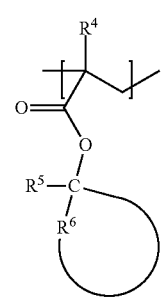

(9)

(wherein $R^4$ represents a hydrogen atom or a methyl group, $R^5$ represents an alkyl group containing 1 to 4 carbon atoms, and $R^6$ represents a linear or branched alkylene or cycloaliphatic alkylene group containing 5 to 20 carbon atoms)

[Formula 10]

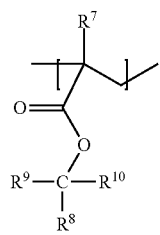

(10)

(wherein $R^7$ represents a hydrogen atom or a methyl group, $R^8$ and $R^9$, which may be the same or different, each independently represent an alkyl group containing 1 to 4 carbon atoms, and $R^{10}$ represents a cycloalkyl or cycloaliphatic alkyl group containing 5 to 20 carbon atoms)

[Formula 11]

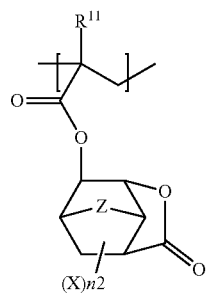

(11)

(wherein $R^{11}$ represents a hydrogen atom or a methyl group, Z represents methylene (—$CH_2$—) or oxa (—O—), each X may be the same or different and represents a hydroxyl group, a halogen group, a nitrile group, a carboxylic acid group, an alkyl carboxylate group containing 1 to 4 carbon atoms, or an alkoxide group containing 1 to 4 carbon atoms, and n2 represents an integer of 0 to 2)

[Formula 12]

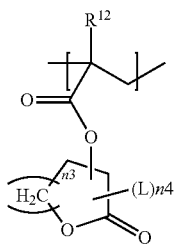

(12)

(wherein $R^{12}$ represents a hydrogen atom or a methyl group, n3 represents an integer of 1 to 3, L represents a methyl group, an ethyl group, a hydroxyl group or a halogen group, and n4 represents 0 to 2).

7. A photosensitive resin composition, which comprises the (meth)acrylic copolymer according to claim 6 and a photoacid generator.

8. A photosensitive resin composition, which comprises the (meth)acrylic copolymer according to claim 5 and a photoacid generator.

* * * * *